(12) United States Patent
Nishiyama et al.

(10) Patent No.: US 10,561,343 B2
(45) Date of Patent: Feb. 18, 2020

(54) INDEX DERIVING DEVICE, WEARABLE DEVICE, AND MOBILE DEVICE

(71) Applicants: Rohm Co., Ltd., Kyoto (JP); THE UNIVERSITY OF TOKYO, Tokyo (JP)

(72) Inventors: Hideki Nishiyama, Kyoto (JP); Tadashi Kobayashi, Kyoto (JP); Senshi Fukashiro, Tokyo (JP)

(73) Assignees: Rohm Co., Ltd., Kyoto (JP); The University of Tokyo, Tokyo (JP)

( * ) Notice: Subject to any disclaimer, the term of this patent is extended or adjusted under 35 U.S.C. 154(b) by 104 days.

(21) Appl. No.: 15/578,734

(22) PCT Filed: May 31, 2016

(86) PCT No.: PCT/JP2016/066050
§ 371 (c)(1),
(2) Date: Dec. 1, 2017

(87) PCT Pub. No.: WO2016/194908
PCT Pub. Date: Dec. 8, 2016

(65) Prior Publication Data
US 2018/0214052 A1 Aug. 2, 2018

(30) Foreign Application Priority Data
Jun. 5, 2015 (JP) .................. 2015114838

(51) Int. Cl.
*A61B 5/11* (2006.01)
*A63B 71/06* (2006.01)
(Continued)

(52) U.S. Cl.
CPC .......... *A61B 5/1116* (2013.01); *A61B 5/1124* (2013.01); *A61B 5/224* (2013.01);
(Continued)

(58) Field of Classification Search
None
See application file for complete search history.

(56) References Cited

U.S. PATENT DOCUMENTS 6,183,365 B1    2/2001  Tonumura et al.
6,973,345 B2 *  12/2005 Yamazaki ............ A61B 5/0537
                                                    600/547
(Continued)

FOREIGN PATENT DOCUMENTS

JP   H09-325081 A    12/1997
JP   2006-263449 A   10/2006
(Continued)

OTHER PUBLICATIONS

Yoshioka, et al, "Computation of kinematics and the minimum peak joint moments of sit-to-stand movements", BioMedical Engineering Online, 6:26, pp. 1-14 (2007).
(Continued)

*Primary Examiner* — Paul M. West
*Assistant Examiner* — Mark A Shabman
(74) *Attorney, Agent, or Firm* — Fish & Richardson P.C.

(57) ABSTRACT

The present invention involves a test subject performing a sit-to-stand (STS) operation while wearing a device (MD) that contains an acceleration sensor (11) on the front of the chest. The present invention derives a muscular strength index (maximum acceleration value per unit of muscle mass during STS activity) representing the muscular strength of a human body by obtaining maximum acceleration value data from a signal expressing the size of an acceleration vector comprising a tri-axial component in detected acceleration, and using the maximum acceleration value data and the muscle mass or body fat mass of the text subject.

14 Claims, 6 Drawing Sheets

(51) Int. Cl.
  *A61B 5/00* (2006.01)
  *A61B 5/22* (2006.01)
  *G01P 7/00* (2006.01)
  *G01P 15/04* (2006.01)
(52) U.S. Cl.
  CPC ............ *A61B 5/681* (2013.01); *A61B 5/7203* (2013.01); *A63B 71/06* (2013.01); *G01P 7/00* (2013.01); *G01P 15/04* (2013.01); *A61B 5/6823* (2013.01); *A61B 5/6824* (2013.01); *A61B 2562/0219* (2013.01)

(56) References Cited

U.S. PATENT DOCUMENTS

| | | | |
|---|---|---|---|
| 2006/0191335 A1* | 8/2006 | Nose | A61B 5/224 73/379.01 |
| 2007/0027369 A1* | 2/2007 | Pagnacco | A61B 5/1071 600/301 |
| 2009/0062627 A1* | 3/2009 | Younger | A63B 24/0003 600/301 |
| 2010/0204615 A1* | 8/2010 | Kyle | A63B 24/0006 600/595 |
| 2010/0211349 A1* | 8/2010 | Flaction | A61B 5/1107 702/141 |
| 2015/0305656 A1 | 10/2015 | Takehara et al. | |

FOREIGN PATENT DOCUMENTS

| | | |
|---|---|---|
| JP | 2006-320533 A | 11/2006 |
| JP | 2009-125506 A | 6/2009 |
| JP | 2012-223452 A | 11/2012 |
| JP | 2015-205133 A | 11/2015 |
| KR | 101189667 B1 | 10/2012 |

OTHER PUBLICATIONS

Japan Patent Office, International Search Report for PCT/JP2016/066050 dated Aug. 23, 2016 (with English translation).

European Patent Office; Extended European Search Report mailed in counterpart European patent application No. 16803342.1 (dated Jan. 2, 2019).

Janssen W G M et al., "Analysis and Decomposition of Accelerometric Signals of Trunk and Thigh Obtained During the Sit-to-Stand Movement," Medical & Biological Engineering & Computing, 43:265-272 Apr. 1, 2005.

MM Gross et al., "Effect of Muscle Strength and Movement Speed on the Biomechanics of Rising From a Chair in Health Elderly and Young Women," Gait & Posture, 8:175-185 Dec. 1, 1998.

Korean Intellectual Property Office; Office Action mailed in counterpart Korean Patent Application No. 10-2017-7033918 (dated Sep. 28, 2019), with English-language Translation.

* cited by examiner

INDEX DERIVING DEVICE, WEARABLE DEVICE, AND MOBILE DEVICE

TECHNICAL FIELD

The present invention relates to index deriving devices, wearable devices, and mobile devices.

BACKGROUND ART

As a movement for estimating the physical strength of a subject, an STS (sit-to-stand) movement is known which is also called a stand-up-from-a-chair movement. An STS movement is a movement that involves moving the center of gravity of the subject's body weight from a comparatively low support base face to a comparatively high position.

In Non-Patent Document 1 identified below, a summary is presented of the relationship among the moments at the hip, knee, and ankle in an STS movement, and it is reported that, irrespective of how the subject stands up in an STS movement, the sum of the moments at the hip and knee in healthy subjects exhibits a constant value (1.53 N·m/kg) and that there is almost no correlation between that sum and the moment at the ankle. It is also reported that, if the sum of the moments at the hip and knee in an STS movement is less than the above-mentioned constant value, a problem is suspected in the subject's ability to stand up, suggesting the necessity for an appropriate exercise therapy to prevent confinement to bed and to motivate to rehabilitation.

NON-PATENT LITERATURE

Non-Patent Document 1: Shinsuke Yoshioka et al., Computation of kinematics and the minimum peak joint moments of sit-to-stand movements, BioMedical Engineering OnLine, 2007, 6:26, pp. 1-14 (accessible at the URL <http://www.biomedical-engineering-online.com/content/6/1/26>).

SUMMARY OF THE INVENTION

Technical Problem

According to the method described in Non-Patent Document 1, reflective markers are placed on the subject's hip and knee respectively, the movement of those parts with the reflective markers in an STS movement is monitored with a high-sensitivity camera, and the moments that act are derived according to equations of motion. Partly because Non-Patent Document 1 is a scholarly article, attempting to build an apparatus that allows measurement of physical strength in some way using the method discussed there requires many devices, making the apparatus expensive (and thus impractical).

Against such backgrounds, the present invention aims to provide an index deriving device, a wearable device, and a mobile device that allows measurement of the physical strength of the human body with a simple configuration.

Means for Solving the Problem

According to one aspect of the present invention, an index deriving device includes: an acceleration sensor for sensing acceleration; and a calculation processor configured to derive a muscular power index as to the muscular power of a human body based on the sensing result from the acceleration sensor.

Specifically, for example, the calculation processor can derive the muscular power index based on an acceleration signal based on the sensing result from the acceleration sensor during an evaluation period in which the human body performs a predetermined movement.

More specifically, for example, the calculation processor can derive the muscular power index by using acceleration maximum value data contained in the acceleration signal.

Further specifically, for example, the calculation processor can derive the muscular power index by using: the acceleration maximum value data, the body weight of the human body, and the body fat percentage of the human body; or the acceleration maximum value data, the body weight of the human body, and the body fat mass of the human body.

For another example, the calculation processor may derive the muscular power index by using: the acceleration maximum value data, the body weight of the human body, and the muscle percentage of the human body; or the acceleration maximum value data and the muscle mass of the human body.

Then, for example, the calculation processor can derive, as the muscular power index, the acceleration maximum value per unit amount of muscle of the human body in the predetermined movement.

For another example, assuming that the acceleration sensed by the acceleration sensor contains an acceleration component due to the movement of the human body and an acceleration component due to gravity, the calculation processor can derive the muscular power index by using the value obtained by subtracting the acceleration component due to gravity from the acceleration maximum value data.

For another example, the acceleration sensor can sense the acceleration along three mutually perpendicular axes individually, and the acceleration signal used to derive the muscular power index can represent the magnitude of the acceleration vector formed by the acceleration along the three axes.

For another example, the predetermined movement can include a movement in which the human body stands up.

According to another aspect of the present invention, a wearable device includes an index deriving device as described above.

According to yet another aspect of the present invention, a mobile device includes an index deriving device as described above.

Advantageous Effects of the Invention

According to the present invention, it is possible to provide an index deriving device, a wearable device, and a mobile device that allows measurement of the physical strength of the human body with a simple configuration.

DESCRIPTION OF EMBODIMENTS

Embodiments of the present invention will be described specifically below with reference to the accompanying drawings. Among the drawings referred to in the course, the same parts are identified by the same reference numerals, and in principle no overlapping description as to the same parts will be repeated. In the present description, for the sake of simple description, symbols and other designations referring to information, signals, physical quantities, components, and the like are occasionally used with the names of the corresponding information, signals, physical quantities, components, and the like omitted or abbreviated.

First Embodiment

A first embodiment of the present invention will be described. This embodiment deals with a measurement device configured to evaluate the muscular strength or the like of a subject in a lightweight and inexpensive fashion (the significance of muscular strength will be discussed later). Whereas the method of Non-Patent Document 1 requires at least two observation points, the measurement device described herein can evaluate muscular strength or the like by use of a single acceleration sensor. It is considered that monitoring equivalent to that performed at two places (hip and knee) in the method according to Non-Patent Document 1 can be performed with a single acceleration sensor appropriately by measuring acceleration at a part of the body that exhibits a correlation with the sum of the hip and knee moments, and as that part of the body, the chest front is most suitable or suitable. On the other hand, in an STS movement, it is important that people stand up vigorously with the power of the lower body alone. Accordingly, the most suitable or a suitable approach is to measure acceleration in a movement of standing up vigorously with the forearms crossed before the chest with an acceleration sensor attached to (for example, kept in close contact with) the subject's arm or chest.

Figure 1A:
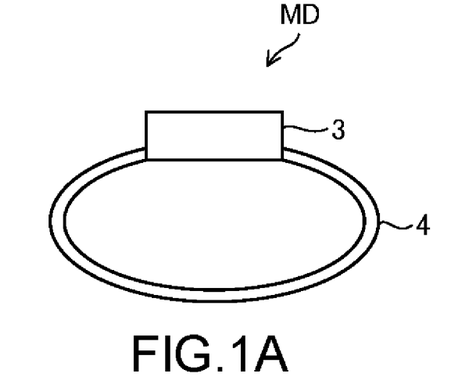
FIGS. 1A and 1B are diagrams showing a structure of a measurement device according to a first embodiment of the present invention.
Figure 1B:
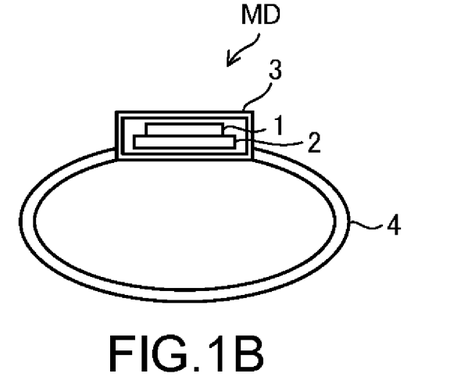

A description will now be given of the structure of a measurement device for measuring muscular strength or the like by use of such a movement. FIG. 1A is an exterior side view of the measurement device MD according to this embodiment. FIG. 1B is a schematic diagram showing the structure inside the housing 3 of the measurement device MD. The measurement device MD includes a component group 1, a circuit board 2, a housing 3, and an attachment band 4. The attachment band 4 may be considered not to be included in the constituent elements of the measurement device MD. On the circuit board 2, electronic components that constitute the component group 1 are mounted. The circuit board 2 having the component group 1 mounted on it is housed in and fastened to the housing 3, which is made of resin or metal and has a predetermined shape. The housing 3 may have any exterior shape; for example, it may have the shape of a cylinder or of a rectangular parallelepiped. Here, for the sake of concrete description, the housing 3 is assumed to have a cylindrical shape.

Figure 2:
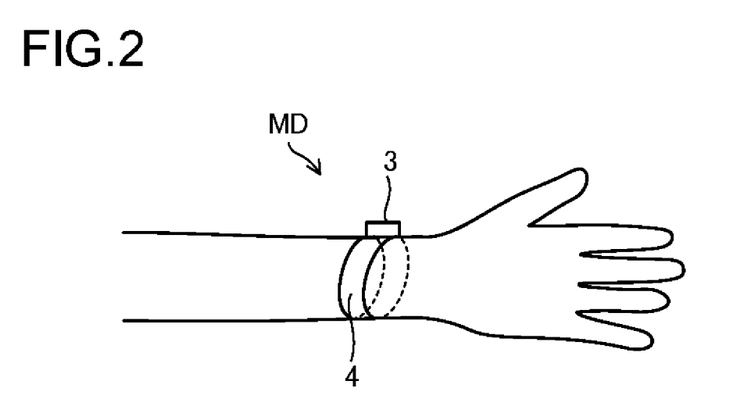
FIG. 2 is a diagram showing the measurement device in FIG. 1A attached to a subject.

The housing 3 is fitted with an attachment band 4 generally in the shape of a ring. The attachment band 4 is formed of, for example, rubber, resin, metal, or a combination of more than one of those. The attachment band 4 is provided to allow the housing 3 having the component group 1 and the circuit board 2 housed in it to be attached and fastened to the human body as a subject. Here, for the sake of concrete description, it is assumed that, as shown in FIG. 2, the measurement device MD is, like a wrist watch or a wrist band, wound around the subject's wrist by use of the attachment band 4. Thus, one face of the housing 3 (one of the bases of the cylindrical shape) is kept in close contact with, and is fastened to, the subject's wrist. It is however also possible, without using the attachment band 4, to keep the housing 3 in close contact with, and fasten it to, the subject's chest such that one face of the housing 3 makes direct contact with the skin of the subject's chest.

Figure 3:
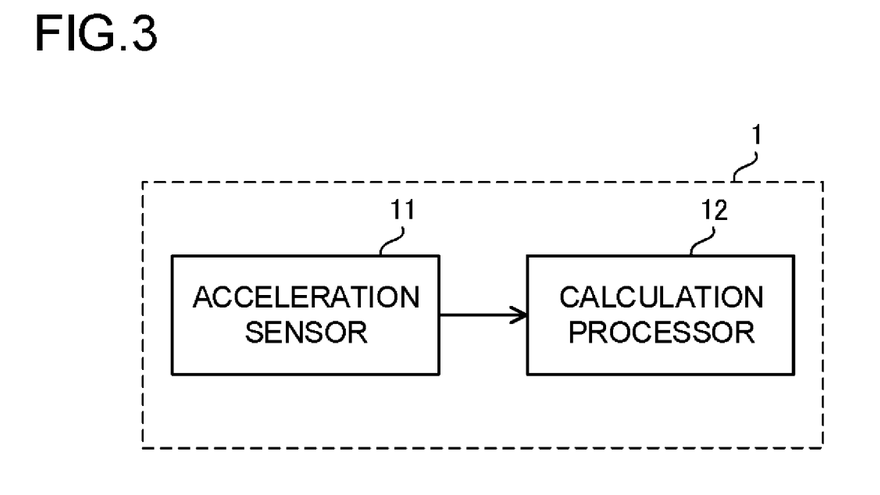
FIG. 3 is a configuration diagram of functional blocks of the measurement device MD in FIG. 1A.

FIG. 3 is a configuration diagram of the component group 1. The component group 1 includes an acceleration sensor 11 and a calculation processor 12. In addition to the components constituting the acceleration sensor 11 and the calculation processor 12, various components can be mounted on the circuit board 2 and housed in the housing 3. Though not expressly illustrated, for example, a power supply circuit for supplying a supply voltage for driving the acceleration sensor 11 and the calculation processor 12 may be mounted on the circuit board 2, and a battery (such as a lithium-ion battery) for supplying electric power to the power supply circuit may be housed in the housing 3.

Figure 4:
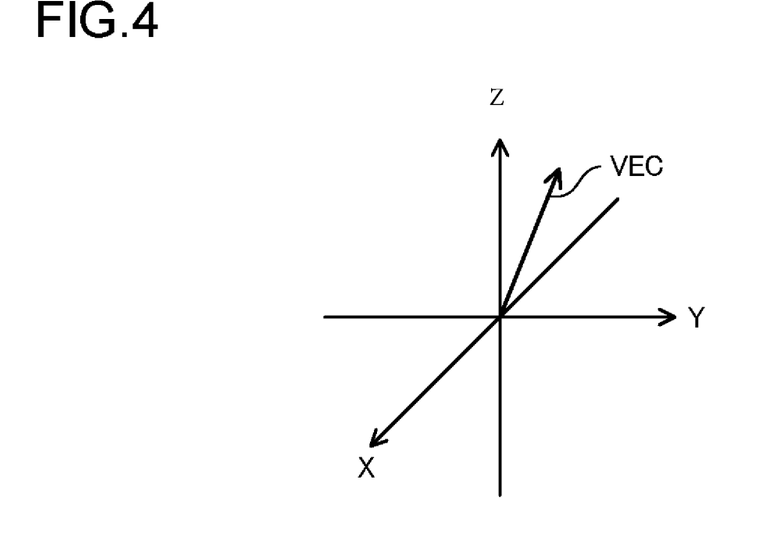
FIG. 4 is a diagram showing the three axes of an acceleration sensor in the measurement device in FIG. 1A along with a sensed acceleration vector.

The acceleration sensor 11 is a three-axis acceleration sensor that senses, in the X-, Y-, and Z-axis directions individually, the acceleration resulting from the acceleration sensor 11 (hence the housing 3 or the measurement device MD) being moved. While the housing 3 is kept in close contact with, and is fastened to, the subject, the acceleration sensor 11 is fixed at a predetermined position inside the housing 3; thus, the acceleration sensed by the acceleration sensor 11 includes the acceleration resulting from the movement (motion) of the subject. As shown in FIG. 4, the X, Y, and Z axes are perpendicular to each other. The acceleration sensor 11 can sense acceleration as a vector quantity, and the acceleration as a vector quantity as sensed by the acceleration sensor 11 is called an acceleration vector. In FIG. 4, a vector VEC represents an acceleration vector formed by acceleration in the X-, Y-, and Z-axis directions. That is, the X-, Y-, and Z-axis components of the acceleration vector are respectively the acceleration in the X-axis direction, the acceleration in the Y-axis direction, and the acceleration in the Z-axis direction as sensed by the acceleration sensor 11.

The calculation processor 12 comprises a microcomputer or the lie, and can estimate and derive the muscular strength or the like of the subject based on the acceleration (hereinafter referred to also as the sensed acceleration) sensed by the acceleration sensor 11. The calculation processor 12 can be formed as a semiconductor integrated circuit.

A description will now be given of a method for estimating and deriving the subject's muscular strength or the like. Based on the sensed acceleration during a predetermined evaluation period including a period in which a subject performs a predetermined evaluation movement, the measurement device MD can estimate and derive the subject's muscular strength or the like.

Figure 5:
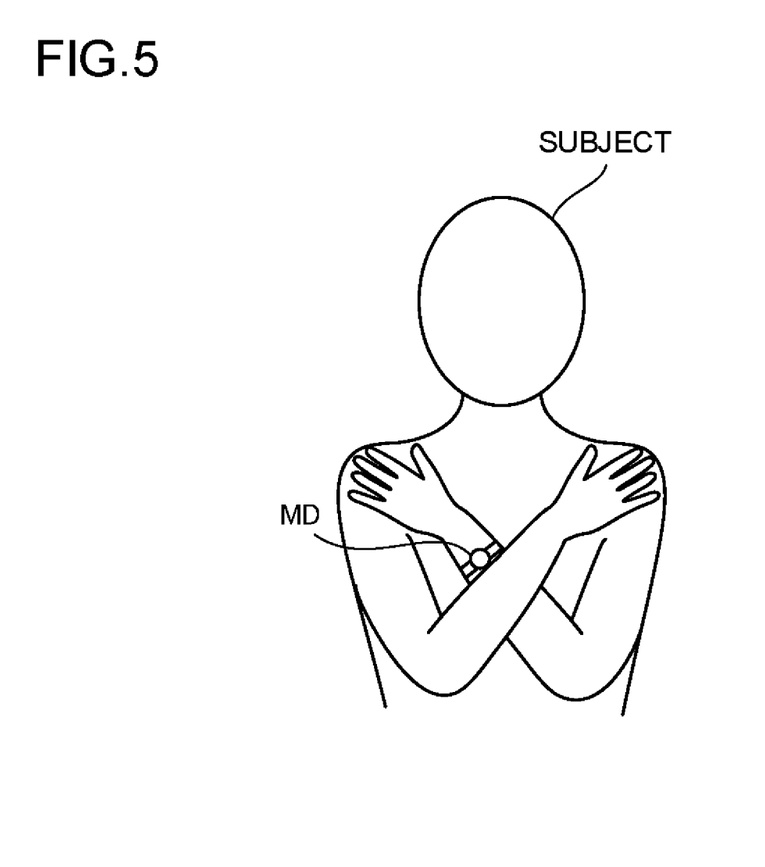
FIG. 5 is a diagram showing a subject standing upright after an evaluation movement.
Figure 6:
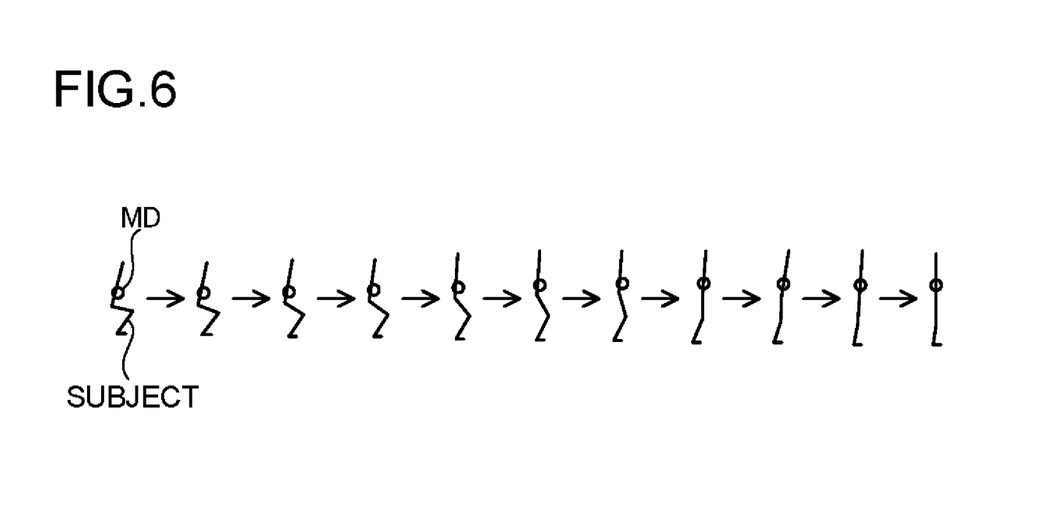
FIG. 6 is a diagram illustrating the evaluation movement.

The evaluation movement is an STS movement in which the subject stands up from a posture seated on the seating face of a chair as a predetermined face to a posture standing upright. The chair may have the seating face at any height; however, with the subject seated on the seating face of the chair, the soles of both feet of the subject should be, at the heels and toes, in contact with the floor. For example, the seating face of the chair has 20% to 30% of the subject's body height. In the evaluation movement, the subject stands up from the seating face of the chair with full force with the forearms crossed before the chest. FIG. 5 is a schematic front view of the subject who has just stood up. FIG. 6 is a simplified schematic side view of the subject during the evaluation period.

In this embodiment, one face of the housing 3 (one of the bases of the cylindrical shape) is kept in contact with, and is fastened to, the subject's wrist. Thus, with the forearms crossed before the chest, the acceleration sensor 11 is located generally in a fixed position before the subject's chest. The evaluation movement may be performed with the housing 3 located in a fixed position such that it makes direct contact with the subject's chest. That is, in the evaluation movement, with the housing 3 having the acceleration sensor 11 housed in it (or the acceleration sensor 11 itself) attached to (for example, kept in close contact with) the subject's arm or chest, the subject stands up with full force from the seating face of the chair.

In an STS movement, acceleration changes chiefly in the vertical direction, and the change of acceleration in the vertical direction includes information reflecting the subject's muscular power. However, depending on how the housing 3 is attached to the subject, the relationship of the X-, Y-, and Z-axis directions in the acceleration sensor 11 with the vertical direction is highly likely to vary in different ways. Accordingly, in the measurement device MD, instead of the acceleration in the X-, Y-, and Z-axis directions being evaluated individually, the magnitude of the acceleration vector is evaluated. The magnitude of an acceleration vector is called an acceleration absolute value, and a signal that has as its signal value an acceleration absolute value is called an acceleration absolute value signal. In this embodiment, unless otherwise stated, an acceleration absolute value is understood as an acceleration absolute value during an evaluation period, and an acceleration absolute value signal is understood as a signal that has as its signal value an acceleration absolute value during an evaluation period.

Figure 7:
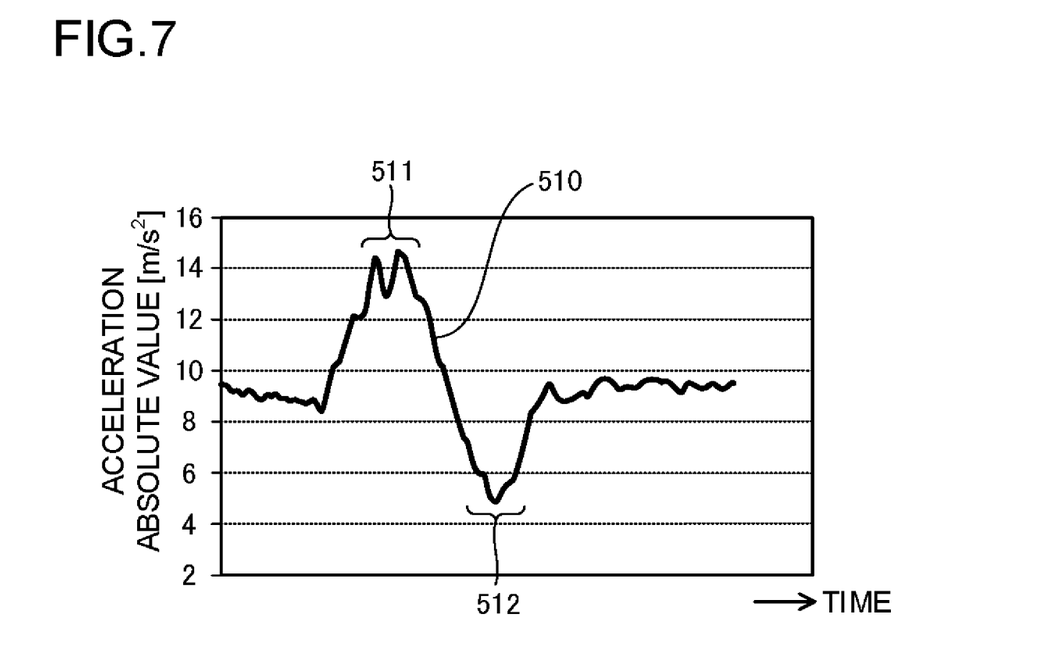
FIG. 7 is a waveform diagram of an acceleration absolute value signal based on a sensing result from the acceleration sensor.

FIG. 7 shows the waveform of an acceleration absolute value signal 510 observed when a subject performed an evaluation movement (in other words, the signal waveform of an acceleration absolute value). In the graph in FIG. 7, the horizontal axis represents time, and the vertical axis represents acceleration absolute value (the same is true with FIG. 8, which will be referred to later). The subject who gave the signal 510 was one of people without any disability, who generally exhibit, in an STS movement, large changes in the acceleration absolute value when the buttocks leave the chair and immediately before the subject halts upright. In FIG. 7, the period in which the signal 511 appears corresponds to the period in which the buttocks leave the chair and, after a while, the period in which the signal 512 appears corresponds to the period immediately before halting upright. Prior to the period in which the signal 511 appears, the period in which the acceleration absolute value remains generally at 9.8 m/s$^2$ is the period before the subject stands up from the chair (for example, the period in which the subject is seated at rest on the chair). The acceleration sensor 11 is configured as a sensor that can sense acceleration due to gravity, and thus, in the period before the subject stands up from the chair (for example, the period in which the subject is seated at rest on the chair), only gravitational acceleration is sensed by the acceleration sensor 11.

In this embodiment, the sampling frequency of the acceleration sensor 11 (that is, the reciprocal of the sensing period at which acceleration is sensed periodically) is set at 200 Hz (hertz). The sampling frequency of the acceleration sensor 11 can be set at other than 200 Hz, in which case the filtering described later can be optimized according to the sampling frequency.

Generally, the acceleration sensor 11 is sensitive to extraneous noise; even if the housing 3 is firmly fastened to the chest or arm, it responds, too sensitively, even to clothes rustling and skin movement. With this taken into consideration, in the measurement device MD, the acceleration absolute value signal which represents the very acceleration sensed by the acceleration sensor 11 is subjected to filtering. This filtering is low-pass filtering whereby, of the acceleration absolute value signal, signal components of comparatively low frequencies are attenuated and signal components of comparatively high frequencies are passed. In this embodiment, the filtering involves low-pass filtering using a fourth-order Butterworth low-pass digital filter, and the cutoff frequency of the low-pass filtering is set at 5 Hz.

Figure 8:
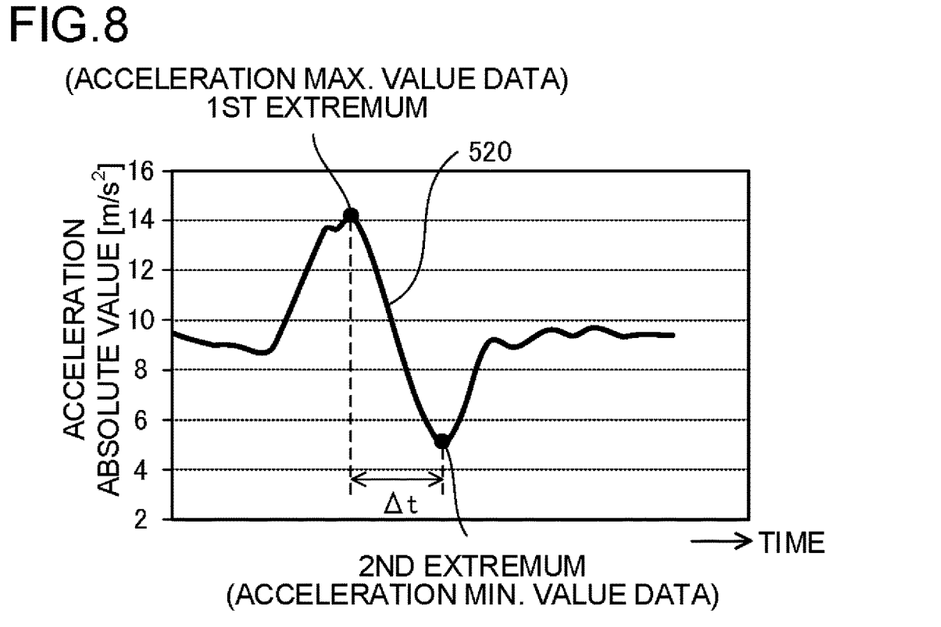
FIG. 8 is a waveform diagram of a signal obtained by applying filtering to the acceleration absolute value signal in FIG. 7.
Figure 9:
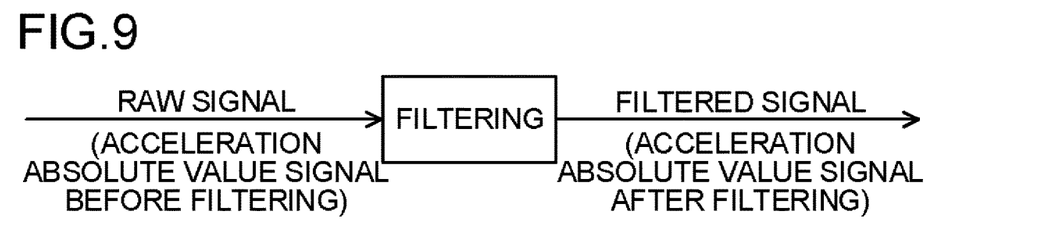
FIG. 9 is a diagram showing a relationship between a raw signal and a filtered signal.

The waveform of the signal obtained by applying filtering to the acceleration absolute value signal 510 shown in FIG. 7, which is the acceleration absolute value signal before filtering, that is, the waveform of the acceleration absolute value signal 520 after filtering, is shown in FIG. 8. In the following description, for the sake of simple and clear description, as shown in FIG. 9, an acceleration absolute value signal before filtering, like the acceleration absolute value signal 510, is called a raw signal, and an acceleration absolute value signal after filtering, like the acceleration absolute value signal 520, is called a filtered signal. The signal value of a raw signal or a filtered signal is an acceleration absolute value.

During the evaluation period, the acceleration absolute value, which is the signal value of the filtered signal, first remains generally at a constant value (9.8 m/s$^2$) and then increases to reach a first extremum around the time point that the subject's buttocks leave the chair; thereafter it decreases to reach the constant value and then further decreases to reach a second extremum around the time point immediately before the subject halts upright; thereafter it increases to reach the constant value.

The first extremum is the maximum signal value of the filtered signal during the evaluation period, and is called the acceleration maximum value data. In the example shown in FIG. 8, the acceleration maximum value data is about 14.3 m/s$^2$. The second extremum is the minimum signal value of the filtered signal during the evaluation period, and is called the acceleration minimum value data. In the example shown in FIG. 8, the acceleration minimum value data is about 5.0 m/s$^2$. For the filtered signal, the time difference between the time point that the signal value equals the first extremum and the time point that the signal value equals the second extremum is represented by Δt (the use of Δt will be discussed later).

The sensed acceleration from the acceleration sensor 11 contains a static component and an inertial component. The static component contains an acceleration component due to gravity and an acceleration component due to an extraneous force other than the subject's movement. Here, it is assumed that the measurement device MD is used on the Earth, and that the magnitude of the acceleration component due to gravity equals 9.8 m/s². Needless to say, gravitational acceleration acts in the vertical direction. The inertial component is an acceleration component due to the subject's movement, and is the necessary component in the STS movement. In an ordinary STS movement, it is considered that no extraneous force is acting and that gravitation is constant; thus, the inertial component can be considered equal to the sensed acceleration minus the acceleration component due to gravity.

The calculation processor 12 includes a filter (unillustrated) that applies filtering to the raw signal to generate the filtered signal, and derives, based on the filtered signal based on the raw signal during the evaluation period, various indices related to the subject's muscular power or the like. The filter may be, instead of being provided in the calculation processor 12, inserted between the acceleration sensor 11 and the calculation processor 12.

[Deriving Index $P_1$]

The indices derived based on the filtered signal can include index $P_1$. Index $P_1$ is given by, for example, $P_1$=(Acceleration Maximum Value Data−Gravitational Acceleration)/(Body Weight×Muscle Percentage), that is, $$P_1=(ACC_{MAX}-9.8)/(WEIGHT \times MS_{PER}). \quad (1A)$$

Here, $ACC_{MAX}$ represents the acceleration maximum value data in the unit of m/s², WEIGHT represents the subject's body weight, and $MS_{PER}$ represents the subject's muscle percentage. Since the subject's muscle percentage indicates the proportion of the subject's muscle mass in the subject's body weight, index $P_1$ can be expressed also as $P_1$=(Acceleration Maximum Value Data−Gravitational Acceleration)/Muscle Mass.

That is, formula (1A) can be rewritten as formula (1B) below:

$$P_1=(ACC_{MAX}-9.8)/MS_{AMT}. \quad (1B)$$

Here, $MS_{AMT}$ represents the subject's muscle mass (that is, the weight of the muscle contained in the subject's body).

The calculation processor 12 can derive index $P_1$ according to formula (1A) or (1B). It is assumed that, when index $P_1$ is derived according to formula (1A) or (1B), the subject's body weight WEIGHT and muscle percentage $MS_{PER}$, or the subject's muscle mass $MS_{AMT}$, has previously been fed to the calculation processor 12.

Inconveniently, it is generally not easy to know an accurate muscle percentage or muscle mass. If, however, we assume that the human body is formed of "muscle", "fat", and "bone and organs" and that the "bone and organs" are constant among subjects irrespective of differences in their physical constitution, then it is possible to derive index $P_1$ by using, instead of a muscle percentage or muscle mass, a body fat percentage or body fat mass, which is comparatively easy to measure and acquire.

Specifically, for example, the calculation processor 12 can derive index $P_1$ according to formula (2A) or (2B).

$$P_1=(ACC_{MAX}-9.8)/WEIGHT \times (1-BF_{PER}) \quad (2A)$$

$$P_1=(ACC_{MAX}-9.8)/(WEIGHT-BF_{AMT}) \quad (2B)$$

Here, $BF_{PER}$ represents the subject's body fat percentage, and $BF_{AMT}$ represents the subject's body fat mass (that is, the weight of the body fat contained in the subject's body). Thus, in formulae (2A) and (2B), for the sake of simplicity, the weight of "bone and organs" is ignored. It is assumed that, when index $P_1$ is derived according to formula (2A) or (2B), the subject's body weight WEIGHT and body fat percentage $BF_{PER}$, or the subject's body weight WEIGHT and body fat mass $BF_{AMT}$, have previously been fed to the calculation processor 12.

For another example, the calculation processor 12 can derive index $P_1$ according to formula (2C) or (2D).

$$P_1=(ACC_{MAX}-9.8)/WEIGHT \times (1-BF_{PER}-K_{A1}) \quad (2C)$$

$$P_1=(ACC_{MAX}-9.8)/(WEIGHT-BF_{AMT}-K_{A2}) \quad (2D)$$

Here, $K_{A1}$ represents a value that is previously defined as indicating the ratio of the weight of the "bone and organs" contained in the subject's body to the subject's body weight. $K_{A2}$ represents a value that is previously defined as indicating the weight of the "bone and organs" contained in the subject's body. Also here, it is assumed that, when index $P_1$ is derived according to formula (2C) or (2D), the subject's body weight WEIGHT and body fat percentage $BF_{PER}$, or the subject's body weight WEIGHT and body fat mass $BF_{AMT}$, have previously been fed to the calculation processor 12.

In formulae (1A), (1B), and (2A) to (2D), the denominator in the right-hand side represents the subject's muscle mass itself or an approximate value of the subject's muscle mass. Thus, index $P_1$ represents the acceleration maximum value per unit amount of muscle of a subject in an STS movement as an evaluation movement, and this is called the muscular strength. The muscular strength depends on the subject's muscular power, and thus can be grasped as an index related to the subject's muscular power (a muscular power index). The muscular power divides roughly into the power of those muscles which work on a continuous basis and the power of those muscles which work on an instantaneous basis (that is, explosive power), and the muscular power based on the result of acceleration sensing is considered to belong to the latter.

Index $P_1$ can be grasped as indicating the efficiency of use of muscles rather than the magnitude of the muscle mass. That is, a high index $P_1$ indicates efficient use of muscles; thus, a high index $P_1$ can be taken as pointing to an excellent muscular strength. For example, even apparently well-muscled people, if they exhibit a low index $P_1$, may not be using their muscles efficiently. In a case where index $P_1$ is derived according to, for example, formula (2A) or the like, it is more difficult for people with comparatively heavy body weights or with comparatively low body fat percentages than for other people to attain a high index $P_1$. In that case, for people with comparatively heavy body weights or with comparatively low body fat percentages to yield excellent results with respect to index $P_1$, they need to attain higher acceleration maximum values than other people (that is, they need to stand up more quickly).

Figure 10:
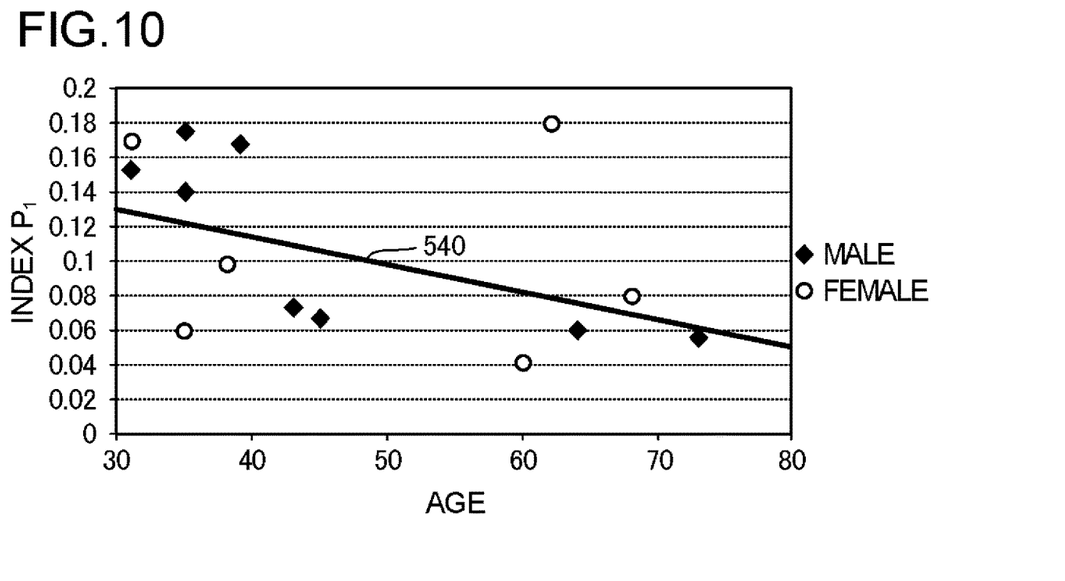
FIG. 10 is a diagram showing a distribution of indices ($P_1$) derived for a plurality of subjects, with age along the horizontal axis.

FIG. 10 shows the results of experiments conducted in connection with index $P_1$. In these experiments, a plurality of subjects performed an evaluation movement, and for each subject, index $P_1$ was derived in the manner described above. Index $P_1$ was derived according to formula (2A). In FIG. 10, the subjects' age is taken along the horizontal axis, and the derived index $P_1$ is taken along the vertical axis. Of the plurality of subjects, eight were male and six were female, and their ages spanned widely from thirties to seventies. In FIG. 10, black diamonds correspond to male subjects, and hollow circles correspond to female subjects (the same is true with FIG. 11, which will be referred to later). The experiments reveal that, at or over a predetermined age (for example, 30), as the subjects' age increases, index $P_1$ tends to decrease. This tendency is considered to reflect the actual tendency of the muscular power declining with increasing age. Also from this fact, it is seen that index $P_1$ is an adequate indicator of the condition of the muscular power of subjects.

In FIG. 10, a straight line 540 represents the average values of index $P_1$ at different ages in the experiments, and is expressed by the formula y=ax+b. In this formula, y represents the value of index $P_1$, x represents the subject's age, and a and b are the coefficients that define the straight line 540. Finding the straight line 540 through the experiments described above with a larger number of subjects can bring the values of the coefficients a and b closer to those which reflect actualities. Although, here, y is taken as a linear function of x, it is also possible to take y as a high-degree function (quadratic or higher-degree function) of x.

[Deriving Index $P_2$]

The indices derived based on the filtered signal can include index $P_2$. Index $P_2$ is given by, for example, $P_2$=(Acceleration Maximum Value Data−Gravitational Acceleration)/(Body Weight×Body Fat Percentage), that is, $$P_2=(ACC_{MAX}-9.8)/(WEIGHT \times BF_{PER}). \quad (3A)$$

Here, $ACC_{MAX}$ represents the acceleration maximum value data in the unit of m/s², and the subject's body fat percentage $BF_{PER}$ is the proportion of the subject's body fat mass in the subject's body weight WEIGHT. Thus, index $P_2$ can be expressed also as $P_2$=(Acceleration Maximum Value Data−Gravitational Acceleration)/Body Fat Mass.

That is, formula (3A) can be rewritten as formula (3B) below:

$$P_2=(ACC_{MAX}-9.8)/BF_{AMT}. \quad (3B)$$

The calculation processor 12 can derive index $P_2$ according to formula (3A) or (3B). It is assumed that, when index $P_2$ is derived according to formula (3A) or (3B), the subject's body weight WEIGHT and body fat percentage $BF_{PER}$, or the subject's body fat mass $BF_{AMT}$, has previously been fed in the calculation processor 12.

Index $P_2$ represents the acceleration maximum value per unit amount of body fat of a subject in an STS movement as an evaluation movement. Generally, it is easier for thin, well-muscled people than other people to attain a high index $P_2$. Thus, index $P_2$ can be used as an indicator of tendency toward obesity.

Figure 11:
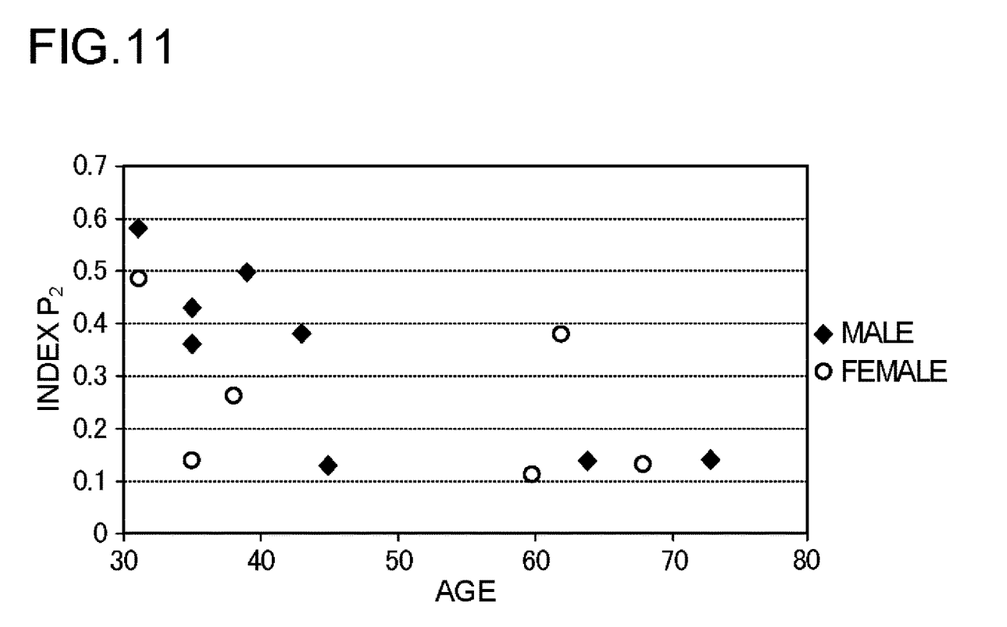
FIG. 11 is a diagram showing a distribution of indices ($P_2$) derived for a plurality of subjects, with age along the horizontal axis.

FIG. 11 shows the indices $P_2$ derived for the plurality of subjects based on the acceleration maximum value data obtained through the above-described experiments corresponding to FIG. 10. In FIG. 11, the subjects' age is taken along the horizontal axis, and the derived index $P_2$ is taken along the vertical axis. Handling similar to that applied to index $P_1$ can be applied to index $P_2$; it is thereby possible to derive, from the indices $P_2$ found for the plurality of subjects, a relational equation between their age and index $P_2$.

[Deriving Index $P_3$]

The indices derived based on the filtered signal can include index $P_3$. Index $P_3$ is derived based on the waveform of the filtered signal during the evaluation period. For example, index $P_3$ is calculated according to formula (4A), (4B), or (4C) below.

$$P_3=k_{B1}(ACC_{MAX}-9.8)-k_{B2} \cdot \Delta t \quad (4A)$$

$$P_3=k_{B1}(ACC_{MAX}-9.8)/\Delta t \quad (4B)$$

$$P_3=k_{B1}/\Delta t \quad (4C)$$

The symbols $k_{B1}$ and $k_{B2}$ represent previously defined positive coefficients. What $\Delta t$ represents is as mentioned above with reference to FIG. 8. It is considered that, the higher the subjects' muscular power (explosive power) is, and thus the quicker they stand up, the greater the acceleration maximum value data $ACC_{MAX}$, and the shorter the time $\Delta t$. Accordingly, like index $P_1$, index $P_3$ too depends on the subject's muscular power, and thus can be grasped as an index related to the subject's muscular power (a muscular power index).

[Collecting Experiment Data]

By use of the measurement device MD, experiment data collection can be performed in a manner as described below. Experiment data collection is performed, for example, at the stage of design or manufacture of the measurement device MD before it is, as a product, used by consumers (general consumers and care-taking and medical professionals). Experiment data collection involves repeating unit experiments. In a unit experiment, one subject of a given age performs an evaluation movement, and for this subject, indices $P_1$, $P_2$, and $P_3$ are derived in the manners described above. Similar unit experiments are conducted with a large number of subjects of varying ages.

A first to an nth age group are defined such that they are mutually exclusive. Here, it is assumed that n is an integer of 2 or more, and that, for any integer i, the ages belonging to the (i+1)th age group are higher than those belonging to the ith age group.

As to a plurality of indices $P_1$ derived for a plurality of subjects belonging to the ith age group, the average value and the positive square root of the dispersion are represented by $AVE_{P1}[i]$ and $\sigma_{P1}[i]$ respectively.

As to a plurality of indices $P_2$ derived for a plurality of subjects belonging to the ith age group, the average value and the positive square root of the dispersion are represented by $AVE_{P2}[i]$ and $\sigma_{P2}[i]$ respectively.

As to a plurality of indices $P_3$ derived for a plurality of subjects belonging to the ith age group, the average value and the positive square root of the dispersion are represented by $AVE_{P3}[i]$ and $\sigma_{P3}[i]$ respectively.

In experiment data collection, from the results of unit experiments with a large number of subjects, a set of classification data (classification data set) is derived which comprises $AVE_{P1}[1]$ to $AVE_{P1}[n]$, $\sigma_{P1}[1]$ to $\sigma_{P1}[n]$, $AVE_{P2}[1]$ to $AVE_{P2}[n]$, $\sigma_{P2}[1]$ to $\sigma_{P2}[n]$, $AVE_{P3}[1]$ to $AVE_{P3}[n]$, and $\sigma_{P3}[1]$ to $\sigma_{P3}[n]$. The calculations for deriving the classification data set may be performed in a calculation device (unillustrated) separate from the measurement device MD.

The classification data set can be derived separately for males and females. In the following description, however, for the sake of simple description, unless otherwise stated, it is supposed that all subjects are male and the classification data set is one for males.

[Specific Example of Use of the Measurement Device]

Figure 12:
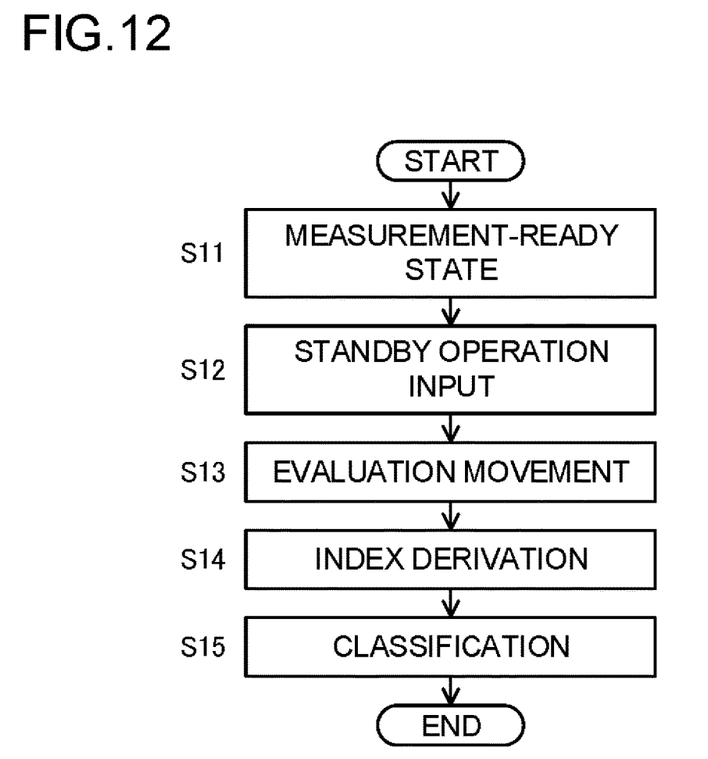
FIG. 12 is a diagram showing a specific flow of an example of use of the measurement device.

With reference to FIG. 12, a description will now be given of a specific flow of an example of how the measurement device MD is used, including how the classification data set is used. The operations at steps S11 through S15 in FIG. 12 are performed after a classification data set is acquired.

First, at step S11, a subject and the measurement device MD are brought into a measurement-ready state. In the measurement-ready state, the subject is seated on a predetermined chair, and one face of the housing 3 of the measurement device MD is brought into contact with, and is fastened to, the subject's wrist (or chest).

Figure 13:
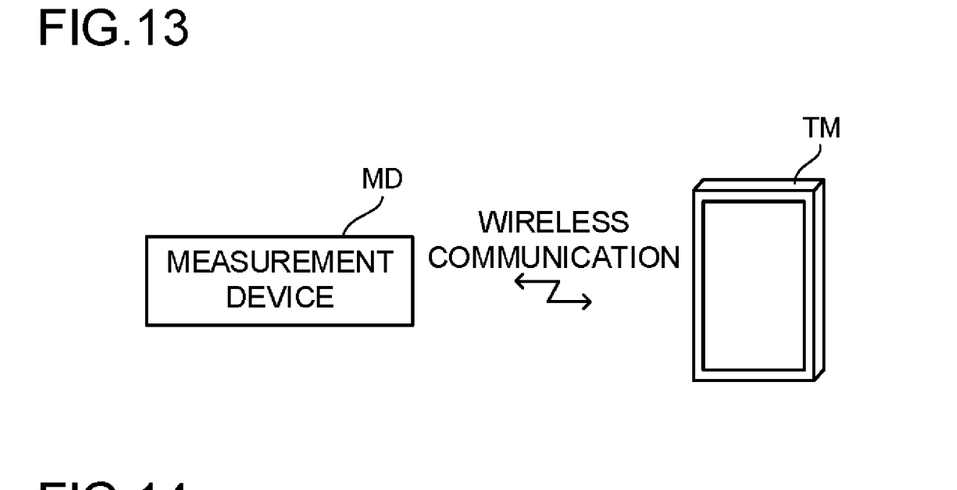
FIG. 13 is a diagram showing the measurement device and a terminal device connected together wirelessly.

Next, at step S12, the subject or another person inputs a standby operation to the measurement device MD. The measurement device MD can recognize whether or not a standby operation has been input. The standby operation is, for example, an operation of pressing an unillustrated operation button provided on the housing 3. In this case, the measurement device MD has only to monitor whether the operation button is depressed. The operation button may be one on a touch panel. For another example, the standby operation may be inputting a predetermined operation to the terminal device TM (see FIG. 13) which is wirelessly connected to the measurement device MD. In this case, on receiving the input of the predetermined operation, the terminal device TM conveys the event to the measurement device MD, and thereby the input of the standby operation is recognized. The measurement device MD and the terminal device TM each include a wireless processor (wireless module), and can exchange any information wirelessly by using those wireless processors. The terminal device TM is, for example, an information terminal, mobile telephone, or personal computer. So-called smartphones belong to information terminals, mobile telephones, or personal computers.

After or before the input of the standby operation, the subject assumes a posture with the forearms crossed before the chest. Promptly after the input of the standby operation, at step S13, the subject performs the evaluation movement described above. The calculation processor 12 can take the time point of the input of the standby operation as the time point of the start of the evaluation period. The evaluation period can have a predetermined length of time (for example, 10 seconds). In this case, the calculation processor 12 takes the time point that a predetermined time has elapsed from the time point of the input of the standby operation as the time point of the end of the evaluation period. For another example, the evaluation period may be ended at the time point at which the acceleration minimum value data is observed in the filtered signal.

After the expiry of the evaluation period, at step S14, based on the sensing result from the acceleration sensor 11 during the evaluation period, the calculation processor 12 derives all or part of indices $P_1$ to $P_3$ described above. Then, at step S15, the calculation processor 12 performs classification based on the indices derived at step S14 and the classification data set. The following description of classification assumes that the classification data set is previously stored in a non-volatile memory (unillustrated) incorporated in the calculation processor 12.

Consider, for example, a case where a subject's age belongs to the ith age group (where i is an integer of 1 or more but n or less). Information that the subject's age belongs to the ith age group has previously been fed to the measurement device MD.

Figure 14:
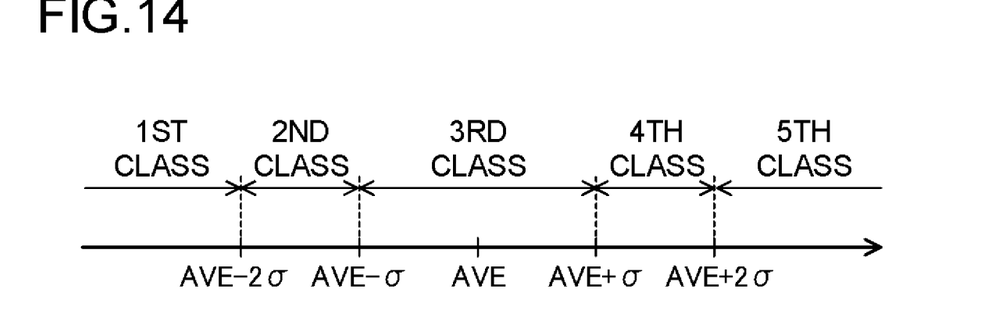
FIG. 14 is a diagram illustrating classification.

In this case, for example as shown in FIG. 14, in classification as to index $P_1$ derived at step S14, with respect to a given index $P_1$, if it fulfills $$P_1 < AVE_{P1}[i] - 2 \cdot \sigma_{P1}[i],$$

it is sorted into a first class; if it fulfills $$AVE_{P1}[i] - 2 \cdot \sigma_{P1}[i] \le P_1 \le AVE_{P1}[i] - \sigma_{P1}[i],$$

it is sorted into a second class; if it fulfills $$AVE_{P1}[i] - \sigma_{P1}[i] < P_1 < AVE_{P1}[i] + \sigma_{P1}[i],$$

it is sorted into a third class; if it fulfills $$AVE_{P1}[i] + \sigma_{P1}[i] \le P_1 \le AVE_{P1}[i] + 2 \cdot \sigma_{P1}[i],$$

it is sorted into a fourth class; and if it fulfills $$AVE_{P1}[i] + 2 \cdot \sigma_{P1}[i] < P_1,$$

it is sorted into a fifth class.

The value ($AVE_{P1}[i] - 2 \cdot \sigma_{P1}[i]$), the value ($AVE_{P1}[i] - \sigma_{P1}[i]$), the value ($AVE_{P1}[i] + \sigma_{P1}[i]$), and the value ($AVE_{P1}[i] + 2 \cdot \sigma_{P1}[i]$) for each age group serve as predetermined reference values in classification as to index $P_1$.

Likewise, for example, in classification as to index $P_2$ derived at step S14, with respect to a given index $P_2$, if it fulfills $$P_2 < AVE_{P2}[i] - 2 \cdot \sigma_{P2}[i],$$

it is sorted into a first class; if it fulfills $$AVE_{P2}[i] - 2 \cdot \sigma_{P2}[i] \le P_2 \le AVE_{P2}[i] - \sigma_{P2}[i],$$

it is sorted into a second class; if it fulfills $$AVE_{P2}[i] - \sigma_{P2}[i] < P_2 < AVE_{P2}[i] + \sigma_{P2}[i],$$

it is sorted into a third class; if it fulfills $$AVE_{P2}[i] + \sigma_{P2}[i] \le P_2 \le AVE_{P2}[i] + 2 \cdot \sigma_{P2}[i],$$

it is sorted into a fourth class; and if it fulfills $$AVE_{P2}[i] + 2\, \sigma_{P2}[i] < P_2,$$

it is sorted into a fifth class.

The value ($AVE_{P2}[i] - 2 \cdot \sigma_{P2}[i]$), the value ($AVE_{P2}[i] - \sigma_{P2}[i]$), the value ($AVE_{P2}[i] + \sigma_{P2}[i]$), and the value ($AVE_{P2}[i] + 2 \cdot \sigma_{P2}[i]$) for each age group serve as predetermined reference values in classification as to index $P_2$.

Likewise, for example, in classification as to index $P_3$ derived at step S14, with respect to a given index $P_3$, if it fulfills $$P_3 < AVE_{P3}[i] - 2 \cdot \sigma_{P3}[i],$$

it is sorted into a first class; if it fulfills $$AVE_{P3}[i] - 2 \cdot \sigma_{P3}[i] \le P_3 \le AVE_{P3}[i] - \sigma_{P3}[i],$$

it is sorted into a second class; if it fulfills $$AVE_{P3}[i] - \sigma_{P3}[i] < P_3 < AVE_{P3}[i] + \sigma_{P3}[i],$$

it is sorted into a third class; if it fulfills $$AVE_{P3}[i] + \sigma_{P3}[i] \le P_3 \le AVE_{P3}[i] + 2 \cdot \sigma_{P3}[i],$$

it is sorted into a fourth class; and if it fulfills $$AVE_{P3}[i] + 2 \cdot \sigma_{P3}[i] < P_3,$$

it is sorted into a fifth class.

The value ($AVE_{P3}[i] - 2 \cdot \sigma_{P3}[i]$), the value ($AVE_{P3}[i] - \sigma_{P3}[i]$), the value ($AVE_{P3}[i] + \sigma_{P3}[i]$) and the value ($AVE_{P3}[i] + 2 \cdot \sigma_{P3}[i]$) for each age group serve as predetermined reference values in classification as to index $P_3$.

Any information recognizable by the measurement device MD, including what is derived at step S14 and what results from the classification at step S15, may be transmitted wirelessly from the measurement device MD to the terminal device TM, or may be displayed on a display screen comprising a liquid crystal display panel or the like. Here, the display screen may be one that can be provided on the housing 3 of the measurement device MD, or may be one provided on the terminal device TM. What is displayed on the display screen is controlled by a display controller (unillustrated) provided in the measurement device MD or in the terminal device TM.

For example, when an index $P_1$ is sorted into the third class, an indication of average muscular strength is displayed on the display screen. When an index $P_1$ is sorted into the fourth class, an indication of better-than-average muscular strength is displayed on the display screen. When an index $P_1$ is sorted into the fifth class, an indication of muscular strength still better than the fourth class is displayed on the display screen. When an index $P_1$ is sorted into the second class, an indication of poorer-than-average muscular strength is displayed on the display screen. When an index $P_1$ is sorted into the first class, an indication of muscular strength still poorer than the second class is displayed on the display screen. When an index $P_1$ is sorted into the first or second class, a message recommending an appropriate exercise therapy or the like may be displayed on the display screen. Also for index $P_2$ or $P_3$, what is displayed on the display screen is controlled likewise. Although, in the method described above, classification is performed among five classes, the number of classes for classification may be other than five.

Although, in the example of operation described above, it is assumed that the filtering, the derivation of indices at step S14, and the classification at step S15 are all performed in the measurement device MD, all or part of them may be performed in the terminal device TM. In that case, part or all of the calculation processor 12 is considered to be present in the terminal device TM. In a case where classification is performed on the terminal device TM, the classification data set has previously been fed to the terminal device TM.

In this embodiment, muscular strength or the like can be measured with a simple configuration involving the use of sensing data from an acceleration sensor. The simple configuration contributes to making devices compact and inexpensive. From subjects' (users') perspective, muscular strength or the like can be measured easily by a habitual movement such as standing up from a chair, and thus their muscular power can be visualized easily on a routine basis. It is thus possible to detect a lack of physical exercise, to improve QOL (quality of life), to advise subjects on an adequate amount of exercise and the like to be aimed at so as not to be confined to bed, and hence to improve healthy life expectancy and, consequently, to reduce medical costs.

Second Embodiment

A second embodiment of the present invention will be described. The second embodiment is based on the first embodiment. Accordingly, as to such features of the second embodiment as are given no particular mention, the relevant description given for the first embodiment, unless inconsistent, applies equally to the second embodiment. As to such features of the second embodiment as contradict between the first and second embodiment, their description given for the second embodiment prevails. The second embodiment deals with some modified or applied techniques based on the techniques described in connection with the first embodiment.

An acceleration sensor that does not sense gravitational acceleration may be used as the acceleration sensor 11, in which case, in the relevant formulae noted in connection with the first embodiment, $(ACC_{MAX}-9.8)$ is to be replaced with $ACC_{MAX}$. In that case, both the first and second extrema are maxima; even then, in a similar manner as in the first embodiment, the first extremum is dealt with as the acceleration maximum value data.

In a case where the evaluation movement is supposed to be performed always with the Z axis parallel to the vertical direction, the acceleration sensor 11 may be a one-axis acceleration sensor that senses acceleration only in the Z-axis direction. In that case, the magnitude of the sensed acceleration in the Z-axis direction can readily be dealt with as an acceleration absolute value.

The measurement device MD can be grasped as including an index deriving device comprising an acceleration sensor 11 and a calculation processor which derives an index (for example, $P_1$, $P_2$, or $P_3$) based on the sensing result from the acceleration sensor 11. A wearable device including the index deriving device can be built. The wearable device may further include an attachment member which permits the index deriving device to be attached to the human body as a subject. The measurement device MD according to the first embodiment is a kind of wearable device, and the attachment band 4 corresponds to the attachment member. The attachment member is not limited to an attachment band 4, but may be anything that permits the index deriving device to be attached to the human body as a subject.

The index deriving device may be incorporated in a mobile device such as a mobile telephone or a smartphone. In that case, the evaluation movement can be performed with the mobile device held in the palm such that it remains in a fixed position before the chest. A wearable device can be grasped as a kind of mobile device. A mobile device includes a component group 1, and the circuit board and the housing constituting the mobile device serve as the circuit board 2 and the housing 3. A mobile device includes a display screen which can display any information (including the indices $P_1$ to $P_3$ derived by the index deriving device), a communication unit which can communicate with another information device via a network such as the Internet, an audio output unit which comprises a loudspeaker and the like that can output audio, a telephony unit which achieves speech communication with a partner device, and the like. A mobile device is often provided with an acceleration sensor for sensing the inclination or the like of the mobile device, in which case the acceleration sensor for sensing the inclination or the like of the mobile device may be used to double as the acceleration sensor 11. The processing to be performed by the calculation processor 12 can then be performed by the microcomputer provided in the mobile device.

When the evaluation movement is performed, the acceleration sensor 11 is placed at a predetermined position where it can sense the acceleration resulting from the subject's movement, and, in the above description, the predetermined position is assumed to be before the subject's chest. This, however, is not meant to limit the predetermined position to before the subject's chest; the predetermined position may instead be before the pit of the stomach, or before the throat, of the subject.

A target device according to the present invention (an index deriving device, a wearable device, or a mobile device) can be built as hardware, such as an integrated circuit, or as a combination of hardware and software. Arbitrary particular functions, which are all or part of the functions performable by the target device, may be written in a program, and this program may be stored in a flash memory that can be mounted on the target device so that, when the program is run on a program execution device (for example, a microcomputer that can be mounted on the target device), those particular functions will be performed. The program can be stored in or fixed to any recording medium. The recording medium in or to which the program is stored or fixed may be mounted on or connected to a device (such as a server device) separate from the target device.

<<Study on the Present Invention>>

To follow is a study on the present invention as implemented in the embodiments described above.

According to one aspect of the present invention, an index deriving device includes: an acceleration sensor (11) for sensing acceleration; and a calculation processor (12) configured to derive a muscular power index (for example, $P_1$ or $P_3$) as to the muscular power of a human body based on the sensing result from the acceleration sensor.

It is thus possible to acquire an index as to muscular power with a simple configuration involving the use of the sensing result from an acceleration sensor. The simple configuration contributes to making devices compact and inexpensive. The compactness and affordability prompt casual use of the devices, and make it easy for the users to visualize their muscular power on a routine basis. It is thus possible to detect a lack of physical exercise, to improve QOL (quality of life), to advise subjects (users) on an adequate amount of exercise and the like to be aimed at so as not to be confined to bed, and hence to improve healthy life expectancy and, consequently, to reduce medical costs.

LIST OF REFERENCE SIGNS

MD measurement device
1 component group
2 circuit board
3 housing
4 attachment band
11 acceleration sensor
12 calculation processor

The invention claimed is:

1. An index deriving device comprising:
an acceleration sensor for sensing acceleration; and
a calculation processor configured to derive a muscular power index as to muscular power of a human body based on an acceleration signal based on a sensing result from the acceleration sensor during an evaluation period in which the human body performs a predetermined movement,
wherein the calculation processor is configured to:
derive the muscular power index by using acceleration maximum value data contained in the acceleration signal, a body weight of the human body, and a body fat percentage of the human body while
increasing a value of the muscular power index as the acceleration maximum value data increases, and
increasing the value of the muscular power index as the body fat percentage of the human body increases, or
derive the muscular power index by using the acceleration maximum value data, the body weight of the human body, and a body fat mass of the human body while
increasing the value of the muscular power index as the acceleration maximum value data increases, and
increasing the value of the muscular power index as the body fat mass of the human body increases.

2. The index deriving device according to claim 1, wherein the calculation processor derives, as the muscular power index, an acceleration maximum value per unit amount of muscle of the human body in the predetermined movement.

3. The index deriving device according to claim 1, wherein the acceleration sensed by the acceleration sensor contains
an acceleration component due to the movement of the human body and
an acceleration component due to gravity, and
the calculation processor derives the muscular power index by using a value obtained by subtracting the acceleration component due to gravity from the acceleration maximum value data.

4. The index deriving device according to claim 1, wherein
the acceleration sensor senses the acceleration along three mutually perpendicular axes individually, and
the acceleration signal used to derive the muscular power index represents magnitude of an acceleration vector formed by the acceleration along the three axes.

5. The index deriving device according to claim 1, wherein the predetermined movement includes a movement in which the human body stands up.

6. A wearable device comprising the index deriving device according to claim 1.

7. A mobile device comprising the index deriving device according to claim 1.

8. An index deriving device comprising:
an acceleration sensor for sensing acceleration; and
a calculation processor configured to derive a muscular power index as to muscular power of a human body based on an acceleration signal based on a sensing result from the acceleration sensor during an evaluation period in which the human body performs a predetermined movement,
wherein the calculation processor is configured to:
derive the muscular power index by using acceleration maximum value data contained in the acceleration signal, a body weight of the human body, and a muscle percentage of the human body while
increasing a value of the muscular power index as the acceleration maximum value data increases, and
decreasing the value of the muscular power index as the muscle percentage of the human body increases, or
derive the muscular power index by using the acceleration maximum value data and a muscle mass of the human body while
increasing the value of the muscular power index as the acceleration maximum value data increases, and
decreasing the value of the muscular power index as the muscle mass of the human body increases.

9. The index deriving device according to claim 8, wherein the calculation processor derives, as the muscular power index, an acceleration maximum value per unit amount of muscle of the human body in the predetermined movement.

10. The index deriving device according to claim 8, wherein
the acceleration sensed by the acceleration sensor contains an acceleration component due to the movement of the human body and an acceleration component due to gravity, and the calculation processor derives the muscular power index by using a value obtained by subtracting the acceleration component due to gravity from the acceleration maximum value data.

11. The index deriving device according to claim 8, wherein the acceleration sensor senses the acceleration along three mutually perpendicular axes individually, and the acceleration signal used to derive the muscular power index represents magnitude of an acceleration vector formed by the acceleration along the three axes.

12. The index deriving device according to claim 8, wherein the predetermined movement includes a movement in which the human body stands up.

13. A wearable device comprising the index deriving device according to claim 8.

14. A mobile device comprising the index deriving device according to claim 8.

* * * * *